Figure 1:
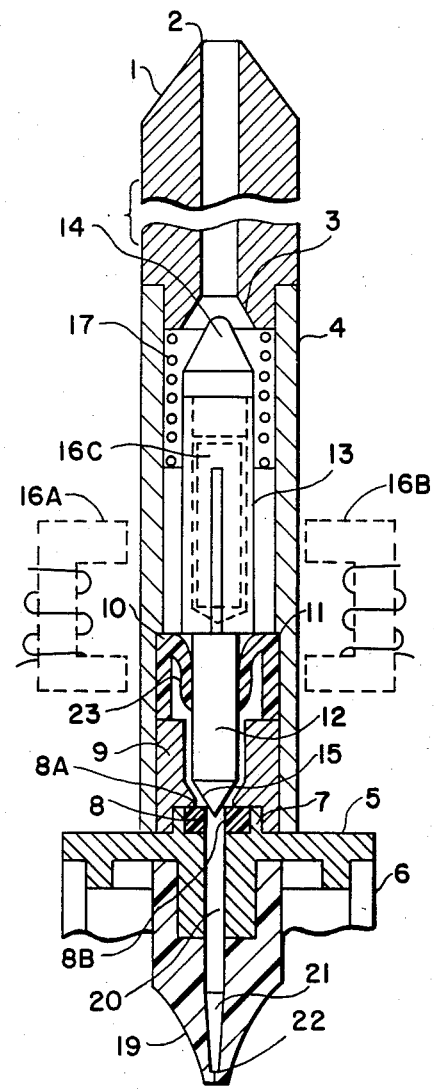

United States Patent [19]

Jones

[11] Patent Number: 4,629,099

[45] Date of Patent: Dec. 16, 1986

[54] ESCAPEMENT DEVICE

[76] Inventor: J. Paul Jones, R.D. 1 Box 171-L, Glenmoore, Pa. 19343

[21] Appl. No.: 769,714

[22] Filed: Aug. 27, 1985

[51] Int. Cl.$^4$ .............................................. G01F 11/32
[52] U.S. Cl. .................................... 222/453; 222/504; 604/249; 604/414; 251/129.21; 137/614.2; 137/844
[58] Field of Search ............ 222/504, 420, 386, 386.5, 222/424.5, 449–451, 453, 490, 494; 604/33, 246, 247, 249, 411, 414, 74; 251/129.21; 137/614.16, 614.2, 844

[56] References Cited

U.S. PATENT DOCUMENTS

| | | | |
|---|---|---|---|
| 2,254,833 | 9/1941 | Ashkenaz | 222/644 |
| 3,072,302 | 1/1963 | Giovannoni et al. | 222/453 |
| 3,199,747 | 8/1965 | Erickson | 222/504 |
| 4,015,755 | 4/1977 | Lerner et al. | 222/442 |

FOREIGN PATENT DOCUMENTS

| | | | |
|---|---|---|---|
| 0499115 | 1/1939 | United Kingdom | 222/453 |
| 1005693 | 9/1965 | United Kingdom | 222/504 |

Primary Examiner—Joseph J. Rolla
Assistant Examiner—Louise S. Heim
Attorney, Agent, or Firm—Frederick J. Olsson

[57] ABSTRACT

An escapement device to be disposed between a source of fluid and a receiver of fluid. The device allows fluid to escape from the source and then intermittently takes a fixed, measured quantity of such fluid and transfers that quantity to the receiver. The device is useful in intravenous infusion systems, automatic blood testing equipment, and like equipment where small but highly accurate measures of fluid are needed.

3 Claims, 2 Drawing Figures

ESCAPEMENT DEVICE

This invention relates in general to fluid control devices and in particular relates to an escapement device to be disposed between a source of fluid and a receiver of fluid and which functions to extract fluid from the source and intermittently transfer identical amounts of fluid to the receiver.

A device of the kind in question allows fluid to escape from the source and then intermittently takes a fixed, measured quantity of such fluid and transfers that quantity to the receiver. The structure of the escapement device will be described in connection with an intervenous infusion sytem. It will be understood, however, that the device finds utility in other environments such as in laboratories where small but accurate measures of fluid are used in blood testing machines and the like.

My copending application Ser. No. 723,563 filed 4/15/85 discloses an escapement device for an intervenous infusion system which includes an escapement cylinder connected between a spike and a drip chamber, a shuttle mounted inside of the escapement cylinder for reciprocating motion up and down along the axis of the cylinder and powered by a magnetic drive means, fluid intake and fluid discharge valve means which are open and/or closed as a function of the shuttle position, together with a one-way stop or check valve. In the application referred to, the shuttle has a fluid control piece which includes a fluid discharge plug forming one part of the fluid discharge valve, the piece is configured to constitute the top of a volumetric or drop forming chamber and functions to allow fluid to flow into the volumetric chamber and to push or discharge the fluid out of the chamber until the fluid discharge plug engages a fluid discharge valve seat which constitutes the other part of the fluid discharge valve.

The invention herein discloses improvements in the fluid control piece, in the fluid discharge plug, and in the fluid discharge valve seat.

The fluid discharge plug herein is formed on the end of an elongated cylindrical stem on the shuttle and is made of hard material and engages with a knife-edge like fluid discharge valve seat formed of softer material, the effect of which is to produce positive fluid cut-off even though a small particale may be stuck on the seat or on the plug. This adapts the escapement device for use with fluids where small particles may be present.

The improved fluid control piece herein is in the form of a reverse-band flexible seal means which is fixed on the escapement cylinder wall and extends inwardly to slidingly engage the cylindrical stem on the shuttle to form the upper end of the drop forming or volumetric chamber, the seal cooperating with the stem in a manner so that fluid cannot flow into the volumetric chamber during the time the drop of fluid is being discharged and, therefore, insuring consistency in the volume of the drops.

The escapement cylinder, the flexible seal, and the cylindrical stem, are arranged to that the distance the shuttle travels to put a given volume of fluid into the volumetric chamber can be made relatively large whereby tolerance of the parts need not be as close as if the distance was substantially shorter.

The cylindrical stem and its fluid discharge plug, the fluid discharge seat means, and the flexible seal all cooperate to permit the tolerances on the various molded parts of the device to be relatively wide which greatly simplifies manufacture and assembly.

In connection with the description herein, it will be apparent that many of the parts are the same as shown in my applications noted following all of which are copending: application Ser. No. 723,563 filed 4/15/85 and entitled "Escapement Device"; application Ser. No. 674,036 filed 11/23/84 and entitled "Plug Valve"; application Ser. No. 674,406 filed 11/23/84 and entitled "Means for Counting Drops"; and application Ser. No. 674,185 filed 11/23/84 and entitled "Linear Impulse Motor". Where applicable, the relevant disclosure of any of said applications is incorporated herein by reference.

Figure 2:
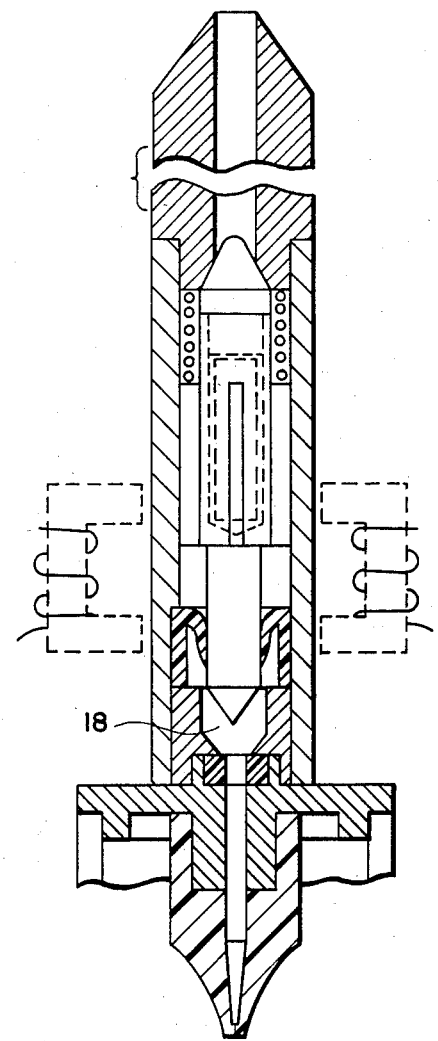

The invention will be described below in connection with the following drawings wherein:

FIG. 1 is an elevational view partially in section and shows the escapement device mounted between the spike and drip chamber of an intervenous system. In FIG. 1, the components are in a first or start position; and FIG. 2 is a view like FIG. 1 except that the components are in a second or momentary stop position.

In an intervenous infusion system the source of fluid conventionally is a plastic bag and the tapered end of a spike is inserted into the bag and receives fluid therefrom. Also, in an intervenous infusion system, the receiver or receiving system includes a drip chamber and a plastic line for carrying fluid from the drip chamber to a needle at the end of the line, which is inserted in the patient's body.

Referring to FIG. 1, in the present arrangement, the spike 1 is formed with a bore 2 and a fluid intake valve seat 3. The spike is fused with the escapement cylinder 4. The escapement cylinder 4 is fused to the cap 5 of the drip chamber 6. Except for the structure of the cap 5, the foregoing correspond to the same named parts in my copending application Ser. No. 723,563.

Disposed in the rim 7 on the cap 5 is a silicon rubber disc 8 which is captured by the escapement cylinder foot 9. The disc 8 is made in accordance with the process noted in my co-pending application Ser. No. 764,036 so that the top surface of the disc is flat and normal to the central aperture 8b and the edge 8a is sharp, uniform, and resilient. The aperture 8b forms a passageway normal to the opening of the escapement cylinder. The edge 8a forms a fluid discharge valve seat.

On top of the foot is the reverse bend, flexible, silicon rubber seal 10 captured on the foot 9 by the shoulder 11 on the escapement cylinder. The seal 10 is firm against the escapement cylinder and extends over to and slidingly engages the cylindrical stem 12 which is an extension of the shuttle 13.

On the top, the shuttle carries a body piece which has a conically shaped surface forming the fluid intake plug 14. The fluid intake plug 14 cooperates with the fluid intake valve seat 3 to form the fluid intake valve $V_i$. The shuttle is like the shuttle shown in my co-pending application Ser. No. 723,563 except for the extension 12.

The cylindrical extension 12 has a conical surface 15 which forms the fluid discharge plug which cooperates with the fluid discharge valve seat 8a.

I will now explain the shuttle drive means.

The drive means includes a pair of U-shaped core/winding assemblies 16a and 16b and permanent magnet 16c mounted within the shuttle. In certain instances the drive may include a compression spring such as spring 17.

The details of component arrangement and of operation of a drive mechanism of the kind in question is shown in my copending application Ser. No. 674,185. Thus, the description herein will concern the components of the drive particularly with respect to moving the shuttle means 13.

Referring to the core/winding assemblies 16a and 16b, it is pointed out that each winding is arranged so that when energized the north and south poles are formed as noted by the letters N and S. In connection with that arrangement the permanent magnet 16c is set up in the shuttle so that its north pole is at the top and the south pole is at the bottom.

As noted in FIGS. 1 and 2, the core/winding assemblies 16a and 16b are disposed respectively on opposite sides of the escapement cylinder 4 with the respective north and south poles facing one another. The cores lie in and are symmetrical with a vertical plane which contains the axis of the escapement cylinder.

In the first position as shown in FIG. 1 the shuttle means 13 positions the lower or south pole of the magnet 16c midway between the north and south poles of the cores. In the up or second position, the shuttle positions the lower or south pole of the magnet 16c in approximate alignment with the north poles of the cores.

The windings are energized by short duration pulses. A pulse is applied when the shuttle is in the first position of FIG. 1 and the reaction with the permanent magnet 16c causes the shuttle to quickly move to the second position of FIG. 2. The drive pulse turns off when the shuttle is in the second position. The stay in the second position is momentary. Thereafter, the position of the south pole of the magnet 16c with respect to the cores causes the magnet to drive the shuttle down to the first position. As previously noted, the down force may be augmented by the use of the spring 17. The spring 17 is compressed when the shuttle is moved up to the second position of FIG. 2, and has a small bias pressure in the first resting position to maintain a good seal.

The core/assemblies 16a and 16b are mounted in a housing not shown. Preferably, the housing is C-shaped and its center aperture is dimensioned to a sliding sideways fit with escapement cylinder 4. The open part of the C-shape permits the spike tip and escapement cylinder to be snapped into position without touching the housing. Touching could cause a possible loss of sterility of the spike. It is also both convenient and necessary to plug the spike 1 into the fluid source first, which would preclude a conventional solenoid coil with a circular aperture which would have to be pierced by the spike.

Referring to FIGS. 1 and 2, the inside of the foot 9, part of the top surface of the disc 8, the seal 10, and the conical surface forming the fluid discharge plug 15 comprise a volumetric chamber 18. As will be apparent, this chamber 18 is closed on the top by the flexible seal 10.

In FIG. 1 the components are in a first or start position. In this position the fluid discharge plug 15 engages the fluid discharge valve seat 8a and no fluid can flow downward past the disc 8. The one-way valve 19 on the cap 5 allows fluid to only flow in a downward direction and will not allow any fluid to flow backward up through the assembly. The valve 19 is like the one-way valve shown in copending application Ser. No. 723,563.

Note that the cap 5 is formed with a drip passageway 20 in communication with the central aperture 8b of the disc 8 and also in communication with exit passage 21 of the valve 19. Fluid exits from the exit passage 21 via the slit 22.

The cylindrical stem 12 and fluid discharge plug 15 are made of Delrin plastic. The plug 15 presents a hard unyielding surface. The fluid discharge valve seat 8a is yieldable since it is formed of silicon rubber. The shuttle drive generates enough downward force so that the plug 15 presses into the sharp edge of the seat 8a. Thus, any small particle stuck on the contact area of the plug or edge will be pressed into the edge or pushed aside so that the particle will not cause a separation between the plug and disc which, if present, could cause leakage and additional unwanted fluid between drops and in effect become a means for forming spurious drops.

The operation of the escapement device to transfer fixed amount of fluid from the source to the receiver will now be described.

Assume that the components are in the first position as shown in FIG. 1. The fluid intake plug 14 is spaced down from the fluid intake valve seat 3 and the fluid discharge plug 15 engages the fluid discharge valve seat 8a to seal off the flow of fluid. Fluid from the source has filled the spike bore 2, and the interior of the escapement cylinder 4 down to the flexible seal 10 and fluid is present in the drip passageway 20 and exit passage 21.

When the components are in the second position (which is a momentary position) as shown in FIG. 2, the fluid intake plug 14 has engaged the fluid intake valve seat 3 to stop the flow of fluid from the source into the escapement cylinder 4. The fluid discharge plug 15 has moved away from the fluid discharge valve seat 8a. The upward motion permits fluid to enter and fill the volumetric chamber 18 as will be explained below.

In the position as shown in FIG. 1, the lip of 23 of the flexible seal 10 is in loose contact with the outer cylindrical surface of the stem 12. When the shuttle is moved upward by the magnetic drive, the upward movement of the stem 12 in effect enlarges the volumetric chamber 18 (compare FIG. 1 and FIG. 2). Since the one-way valve 19 does not allow any fluid to move upward, fluid necessary to fill the chamber 18 flows from the source down between the lip 23 and the cylindrical surface of the stem 12. The fluid lubricates and separates the lip 23 from the surface of the stem 12 allowing complete free movement of the shuttle in the upward direction. The fluid flowing between the lip 23 and the stem 12, of course, fills the volumetric chamber 18.

When the second position is reached by virtue of the fluid intake plug 14 engaging the fluid intake valve seal 3, the lip 23 remains in direct contact with the cylindrical surface of the stem 12. There is no flow from the fluid source in the escapement cylinder because of engagement of the fluid intake plug 14 and the fluid intake valve seat 3 and no flow between the lip 23 and stem 12 into the volumetric chamber.

When the shuttle drive means starts to move the shuttle from the second position down to the first position, the pressure of the fluid under the reverse bend seal 10 increases and presses the lip 23 into tight engagement with the cylindrical surface of the moving stem 12. Consequently, there is a volumetric displacement of the fluid into the volumetric chamber 18 downward through the disc 8, through the passageways 20 and 21 and out through the slit 22 into the drip chamber 6. This displacement ends when the fluid discharge plug 15 engages the fluid discharge valve seat 8a and cuts off all downward flow of fluid until the next cycle.

On the way down the flexible seal 10 functions to create a higher fluid pressure in volumetric chamber 19 than the fluid pressure in the escapement cylinder causing the lip to engage the stem 12 so that no fluid flows from the chamber 18 back up into the escapement cylinder. In this way, no fluid is lost and the volume of each drop is the same.

I claim:

1. In an intervenous infusion system:
   a drip chamber including a cap on the top thereof;
   a connection spike;
   an elongated, hollow escapement cylinder, the bottom end of which is connected to the cap of said drip chamber and the top end of which is connected to said spike to extend vertically upwardly when said drip chamber is mounted for use, the escapement cylinder having an interior capture shoulder;
   elongated shuttle means inside of said escapement cylinder;
   guide means on said shuttle engaging the inside wall of said escapement cylinder mounting the shuttle for reciprocating motion along the axis of the escapement cylinder;
   conically shaped fluid intake plug means connected to and disposed at the top end of said shuttle;
   first means on said cap formed with a cylindrically-shaped rim and a drip passageway to pass fluid, the rim and drip passageway being coaxial with the axis of said escapement cylinder;
   a disc made of silicon rubber in said rim and having a flat top surface and a cylindrically shaped central aperture, the flat top surface being normal to the central aperture;
   and the edge formed by the intersection of the top surface of the disc with the surface of the central aperture of the disc forming a sharp, circular fluid discharge valve seat means and the central aperture of the disc forming a fluid passageway coaxial with the axis of said escapement cylinder;
   a cylindrically-shaped escapement foot mounted on said cap and engaging said rim and said escapement cylinder, the foot having a section extending over said disc to capture the same in said rim;
   a reverse bend flexible seal made of silicon rubber mounted on said foot and engaging said capture shoulder;
   second means on said spike formed with conically-shaped fluid intake valve seat means coaxial with the axis of said escapement cylinder to be engaged and disengaged by said fluid intake plug means;
   a cylindrically shaped stem connected to the shuttle and extending coaxially with said axis;
   a conical surface on the end of said stem and forming a fluid discharge plug means to engage with and discharge from said fluid discharge valve seal means;
   said shuttle means being dimensioned to permit passage of fluid through said escapement cylinder as between said fluid intake valve seat means and said fluid discharge valve seat means;
   said reverse bend flexible seal extending between said escapement cylinder and said cylindrically shaped stem and having an annular lip extending in a direction toward said disc and making a sliding engagement with said cylindrically shaped stem;
   drive means for moving said shuttle from a first position to a second position, the first position being below said second position:
   (a) in the first position said fluid intake plug means being spaced away from said fluid intake valve seat means and said fluid discharge valve plug means engaging said fluid discharge valve seat means;
   (b) in the second position said fluid intake plug means engaging said fluid intake valve seat means and said fluid discharge plug means being spaced away from said fluid discharge valve seat means, said disc, the interior of said foot, and said flexible seal forming a volumetric fluid measuring chamber;
   when said shuttle is moving from said first position up to said second position:
   (a) said flexible seal functioning to permit fluid to flow between said lip and said cylindrical stem and into said volumetric measuring chamber until said fluid intake plug means engages said fluid intake valve seat means;
   when said shuttle is moving from said second position down to said first position:
   (a) the pressure of the fluid in said volumetric measuring chamber being greater that the fluid pressure in the portion of the escapement cylinder above said flexible seal so that said lip is pressed against said cylindrical stem and fluid in said volumetric measuring chamber is pushed out of the volumetric measuring chamber until said fluid discharge plug means engages said fluid discharge seat means and said difference in pressure preventing fluid in the volumetric measuring chamber from flowing back up into the escapement cylinder above said seal; and
   (b) the movement of said fluid intake plug means away from said fluid intake valve means permitting new fluid to flow into said escapement cylinder; and
   check valve means connected to said cap and having an exit passage in series with said drip passageway, the check valve means functioning when the shuttle is moving from said second position down to said first position to permit fluid in the volumetric measuring chamber to flow into said drip chamber and functioning when said shuttle is moving from said first position up to said second position to stop any backflow of fluid into the volumetric chamber.

2. The construction of claim 1 wherein said drive means comprises:
   a cylindrically shaped permanent magnet mounted in said shuttle with the axis of the magnet extending in the direction of motion of the shuttle;
   a pair of U-shaped cores each having pole-forming drive winding thereon, the pair being respectively disposed on opposite sides of said escapement cylinder with the respective north poles when formed facing one another and the respective south poles when formed facing one another and the poles lying in a vertical plane containing the axis of the escapement cylinder; and
   in the first position of said shuttle, the lower end of the cylindrically shaped magnet being vertically positioned substantially at the midpoint between the north and south poles of the core magnets.

3. The construction of claim 2 wherein said drive means includes a compression spring inside of said escapement cylinder, the top end of the spring bearing on said spike and the lower end of the spring bearing on said shuttle, the spring functioning to assist in driving the shuttle from the second down to the first position, and maintaining a sealing pressure under all altitudes of the sealing chamber.

* * * * *